(12) United States Patent
Datta et al.

(10) Patent No.: US 9,365,870 B2
(45) Date of Patent: **\*Jun. 14, 2016**

(54) INTEGRATED PROCESSES FOR ANAEROBIC CONVERSION OF HYDROGEN AND CARBON OXIDES TO ALCOHOL

(71) Applicant: Synata Bio, Inc., Warrenville, IL (US)

(72) Inventors: Rathin Datta, Chicago, IL (US); Steve Calderone, Chicago, IL (US); Loula Sassaris Merkel, Des Plaines, IL (US)

(73) Assignee: SYNATA BIO, INC., Warrenville, IL (US)

( * ) Notice: Subject to any disclaimer, the term of this patent is extended or adjusted under 35 U.S.C. 154(b) by 134 days.

This patent is subject to a terminal disclaimer.

(21) Appl. No.: 13/942,311

(22) Filed: Jul. 15, 2013

(65) Prior Publication Data

US 2014/0228598 A1    Aug. 14, 2014

Related U.S. Application Data

(60) Provisional application No. 61/762,702, filed on Feb. 8, 2013, provisional application No. 61/762,715, filed on Feb. 8, 2013.

(51) Int. Cl.
| | | |
|---|---|---|
| *C12P 7/06* | (2006.01) | |
| *C12P 7/04* | (2006.01) | |
| *C12P 7/16* | (2006.01) | |

(52) U.S. Cl.
CPC . *C12P 7/065* (2013.01); *C12P 7/04* (2013.01); *C12P 7/16* (2013.01); *Y02E 50/10* (2013.01); *Y02E 50/17* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 7,285,402 B2 | 10/2007 | Gaddy et al. | |
| 8,119,378 B2 | 2/2012 | Simpson et al. | |
| 8,383,376 B2 | 2/2013 | Simpson et al. | |
| 2009/0076985 A1 | 3/2009 | Morgan et al. | |
| 2010/0298450 A1* | 11/2010 | Datta et al. | 518/702 |
| 2010/0330640 A1 | 12/2010 | Bell et al. | |
| 2013/0045517 A1* | 2/2013 | Oakley et al. | 435/139 |
| 2013/0087339 A1 | 4/2013 | Foody et al. | |
| 2013/0089905 A1 | 4/2013 | Foody et al. | |

FOREIGN PATENT DOCUMENTS

EP    1303629 B1    4/2003

OTHER PUBLICATIONS van Rossum et al., Catalysis Today 145 (2009) 10-18.*

(Continued)

*Primary Examiner* — Karl J Puttlitz
(74) *Attorney, Agent, or Firm* — Cardinal Law Group

(57) ABSTRACT

Integrated processes are disclosed for reducing the carbon foot print related to the use of non-renewable hydrocarbon gas streams for producing alcohols by anaerobic bioconversion of reformed gas. These processes combine renewable and non-renewable gas sources of hydrogen, carbon monoxide and carbon dioxide to produce alcohol. Thus the invention found a highly a practical way to make use of non-renewable carbon oxide sources while still lowering the carbon footprint of such alcohols produced thereby, especially when combined with corn ethanol production. In the case of motor fuel use, the renewable portion of the alcohol produced in this manner provides a reduction in greenhouse gases by 50% or more when compared to gasoline.

6 Claims, 5 Drawing Sheets

(56) References Cited

OTHER PUBLICATIONS

Chandel et al., "Synthetic Natural Gas (SNG): Technology Environmental Implications, and Economics", Climate Change Policy Partnership, 2009, pp. 1-20.*

Per Tunå, Lund Institute of Technology, "Substitute natural gas from biomass gasification", 2008, pp. 1-65.*

John Laumer, CO2 and The Great Ethanol Spreadsheet Mystery, Aug. 14, 2005. http://www.treehugger.com/renewable-energy/co2-and-the-great-ethanol-spreadsheet-mystery.html.

* cited by examiner

INTEGRATED PROCESSES FOR ANAEROBIC CONVERSION OF HYDROGEN AND CARBON OXIDES TO ALCOHOL

This application claims priority to U.S. Provisional Patent Application 61/762,702 filed Feb. 8, 2013 and U.S. Provisional Patent Application 61/762,715 filed Feb. 8, 2013, which are incorporated by herein by reference in their entirety.

FIELD OF THE INVENTION

This invention pertains to the reduction of CO2 gases generated from processes for the production of chemicals and fuels from renewable and non-renewable carbonaceous feedstocks. More specifically, this invention pertains to an anaerobic conversion of a combination of hydrogen and carbon oxides from non-renewable and renewable sources to produce ethanol, propanol and butanol and higher alcohols.

BACKGROUND

Natural gas is a widely available fuel which is primarily methane. The prices of natural gas has declined in recent years and are expected to possibly remain low for decades, natural gas has become a favored form of energy. As with any hydrocarbon based energy source, questions are raised about its contribution to greenhouse gases.

Greenhouse gases are part of the 'greenhouse effect' that presents an environmental issue associated with the potential for global climate change. A number of gases in our atmosphere regulate the amount of heat retained close to the earth's surface. Water vapor, carbon dioxide, methane, and nitrogen oxides are the most common naturally occurring greenhouse gases. As the concentration of greenhouse gases increase, temperatures throughout the environment will rise significantly.

The continually increasing use of fossil fuels has caused an increase over the naturally occurring amounts of these gases and ways are sought to reduce the man-made influence in the generation of such gases. Carbon dioxide is seen as a major source of greenhouse gas. Even though carbon dioxide has less of an effect on trapping heat than the other naturally occurring gases, its prevalence from the increased reliance on hydrocarbons makes it suspect as a significant contributor to trapping of heat in global warming. For this reason those concerned with climate change are especially interested in limiting the generation of carbon dioxide.

From the standpoint of CO2 production from hydrocarbon usage, natural gas offers important environmental benefits relative to the combustion of other fossil fuels. In rough numbers combustion of treated and unconverted natural gas will produce 30% less $CO_2$ emissions than oil and almost 45% less $CO_2$ emissions than coal. However, methane in the form of an emission is over 20 fold more potent in its greenhouse gas effect than carbon dioxide.

While there are many applications for using natural gas as an energy source in its gas phase, attention has focused on how to utilize this energy source in the most efficient manner. Major drawbacks to the use of natural gas in traditional applications are problems of its storage and transportation as long as it remains in a gas form.

One way in which those seeking increased the natural gas utilization have attempted to overcome these problems is by employing processes for converting natural gas to denser and more easily transportable forms. Natural gas is typically converted into a liquid form by gas to liquid (GTL) processes, the primary of which either produces syncrude that directly converts the gas or produces synthesis gas that indirectly converts the natural gas. Although the combustion of natural gas in the unconverted gaseous form has green-house gas advantages, further processing of natural gas to liquids to transform it to more easily transported forms increases its greenhouse gas impact.

One solution to the problem of CO2 production from industrial processes is to sequester CO2 that is produced by such processes. Effecting carbon dioxide ($CO_2$) capture and sequestration (CCS) has been proposed by various technologies that can reduce $CO_2$ emissions from facilities such as coal-fired and gas-fired power plants, and large industrial sources. Most CCS technologies employ three steps. The first step will capture CO2 from oil refining operations, treatment of well head gas, powerplants, renewable fuel production or other industrial processes. Compression of the captured CO2 prepares it for transfer, in tanks, pipelines or via other means, to permanent sequestration facilities. These facilities usually comprise geologic formation located a mile more underground that hold the CO2 in a porous layer of rock situated beneath a gas impermeable layer of rock. The impermeable layer of rock prevents an upward migration of the CO2. This type of CO2 sequestration is expensive, used infrequently and impractical for major sources of CO2 emissions.

Another major source of CO2 emissions is in the use of hydrocarbons as motor fuels. An approach to reduce the effect of CO2 emissions from hydrocarbon fuel combustion is to produce motor fuels from renewable resources such as plant materials. This approach reduces the use of non-renewable, i.e. fossil, hydrocarbons that when combusted put carbon dioxide into the atmosphere by releasing the fossil hydrocarbons from their naturally sequestered state. In contrast, using renewable sources for feedstocks, i.e. plant materials, maintains a closed CO2 system where the carbon dioxide released by hydrocarbon combustion balances with the carbon dioxide captured by the plant material that goes into the feedstock for producing the fuels and chemicals.

Plant materials for use in such feedstocks can come from almost any plant source. One general type of plant material, such as corn, rice, cane, wheat, sorgum etc., have high carbohydrate concentrations that are readily converted to sugars. At this time essentially all of the production of ethanol for motor fuel purposes relies on the saccharization of plant materials into sugar and its fermentation to alcohols. These fermentations produce CO2 directly as a by-product of the fermentation process. In such processes the amount of CO2 produced directly can equal the mass of ethanol. Moreover, concerns about plant sources can arise since their use requires utilization of land and water resources for growth of these corps or trees and is subject to limitations posed by alternative uses of these land and water resources for food and other agricultural and forest product production.

Another way to produce alcohol motor fuels or other chemicals is by generating syngas from plant material or natural gas. In the case of plant material, its gasification will produce a syngas. In the case of natural gas it may be converted to reformed gas. The syngas obtained by gasification or by conversion of natural gas are suitable substrates for anaerobic fermentations of hydrogen and carbon monoxide. Anaerobic fermentation processes involve the contact of the substrate gas in an aqueous fermentation menstruum with microorganisms capable of generating alcohols such as ethanol, propanol, i-butanol and n-butanol. The production of these alcohols requires significant amounts of carbon monoxide and carbon dioxide together with hydrogen.

In addition to the aforementioned plant and natural gas sources, a suitable source of the substrate gas for carbon monoxide and hydrogen conversions can be derived from the gasification of carbonaceous materials other than those specifically mentioned such as the partial oxidation of natural gas, biogas from anaerobic digestion or landfill gas, coal coking and industrial steel manufacture. The substrate gas containing, carbon monoxide, hydrogen, and carbon dioxide, usually contains other components such as water vapor, nitrogen, methane, ammonia, hydrogen sulfide and the like. (For purposes herein, all gas compositions are reported on a dry basis unless otherwise stated or clear from the context.)

In any of the above cases certain anaerobic bacteria, especially those from the genus *Clostridium* can produce various alcohols, particularly ethanol, from the resulting substrates comprising CO, CO2 and $H_2$ via the acetyl CoA biochemical pathway. Different strains of *Clostridium ljungdahlii* that exemplify producing ethanol from gases are described in WO 00/68407, EP 117309, U.S. Pat. Nos. 5,173,429, 5,593,886, and 6,368,819, WO 98/00558 and WO 02/08438. Abrini et al, Archives of Microbiology 161, pp 345-351 (1994)

The effectiveness of converting CO2 to other products will depend on the amount of CO and H2 that is present with the CO2 in the converted gas stream. For instance, the theoretical equations for the conversion of carbon monoxide and hydrogen to ethanol are:

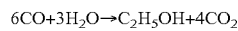

$$6CO+3H_2O \rightarrow C_2H_5OH+4CO_2$$

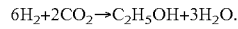

$$6H_2+2CO_2 \rightarrow C_2H_5OH+3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. The microbiological processes that take place have been expressed for convenience in the formulas shown above. It is known that in the microbiological process the production of the alcohol requires a carbon source and a biological energy source. The formulas show that the biological energy source is the available electrons in the hydrogen and carbon monoxide of the substrate gases. As a result gas streams with high CO will produce more CO2 or those with low H2 will limit the conversion of CO2 and in either case may make the anaerobic process a net producer of CO2.

Regardless of originating source, the substrate gases are typically more expensive than equivalent heat content amounts of the carbonaceous feedstock fuel. Hence, a desire exists to use these gases efficiently to make higher value products. The financial viability of any conversion process, especially to commodity chemicals such as ethanol, will depend, in part, upon the costs of the feedstocks, conversion efficiency and operating and capital costs for generating the substrate gases; and upon the capital costs, the efficiency of conversion of the carbon dioxide, carbon monoxide and hydrogen to the sought products, the process energy costs and the extent of the electron availability and utilization to effect the conversion of the substrate gases to the higher value products.

In a bioreactor, hydrogen and carbon oxides pass from the gas phase to being dissolved in the aqueous menstruum, and then the dissolved hydrogen and carbon oxides contact the microorganisms for bioconversion. Due to the low solubilities of carbon monoxide and, especially, hydrogen in aqueous media, mass transfer can be a factor limiting rate and conversion in the bioconversion to alcohol.

The off gases from bioreactors contain substrate that was not bioconverted and diluents such as methane and nitrogen. Although off gases can be recycled to the bioreactor or passed to another bioreactor, challenges can exist. For instance, the substrate gases may contain diluents that, if recycled to a bioreactor, can build-up and reduce the partial pressure, thus reducing the driving forces for mass transfer of hydrogen and carbon monoxide to the aqueous menstruum.

Overall, the net effect of the processing as gas into liquids such as alcohol or hydrocarbons will produce an increase in the $CO_2$ emissions when compared to a liquid to liquid conversion such as petroleum crude to gasoline. No one to date has disclosed a process that can improve the overall greenhouse gas emissions from the processing of natural gas to produce ethanol.

Bell in United States Published Patent Application No. 20100105118 discloses an integrated process for making alcohols from natural gas which provide a high bioconversions of carbon monoxide in fermentations in the absence of oxygen. Bell notes at paragraph 0013 that, in theory, carbon dioxide may be used as a reactant for the production of higher alcohols such as ethanol. However, he states that in practice the fermentation route to higher alcohols tends to be a net producer of carbon dioxide. In his disclosed process, the gas from the bioreactor which contains carbon dioxide is fed to a reaction section of a steam reformer. The reformer is either operated dry or with a mole ratio of water to carbon dioxide of less than 5:1. Bell confirms the low conversion of hydrogen in the examples. Although Bell may have reduced carbon dioxide emissions as compared to the use of autothermal reforming or traditional steam reforming, the low conversion of hydrogen detracts from the commercial viability of the disclosed process.

Processes are therefore sought that can reduce the carbon footprint in the utilization of the non-renewable resources.

Processes are also sought that can reduce emitted greenhouse gases by utilizing CO2 released in the fermentation of renewable resources.

Processes are also sought that can maximize the production and availability of electrons for microorganism growth and alcohol production while also reducing $CO_2$ emissions for the production of alcohol in commercial-scale, continuous operations.

SUMMARY

This invention satisfies the above process needs by providing continuous processes for the anaerobic conversion of hydrogen and carbon oxides to higher alcohols, especially ethanol, propanol and butanol, that integrate the unit operations of fermentation, methane reforming, and renewable alcohol production operation to provide substrate gas from methane that provides over 90% of the available electrons from the methane to the microorganisms and adds an exogenous, and preferably a renewable, source of $CO_2$ to produce alcohol. The process reduces the greenhouse gas impact from utilizing methane as a starting feed for the production of alcohol by incorporating a source of $CO_2$ that is usually vented to the atmosphere, but now instead contains it in a usable form. In particular it has been found that the combination of high conversion and a specific range of electrons to carbon atom ratios ($e^-/C$) of the hydrogen and carbon oxides provides a surprising productivity to higher alcohols and facilitates the use of feed gas substrates comprising mixtures of non-renewable and renewable gas sources to provide higher alcohols with a renewable carbon component. In achieving this effectiveness the processes uses non-oxidative reforming to provide the high availability of electrons from the methane feed. The process is thus arranged and operated in a manner that provides high conversion and efficient processing by combining a high $CO_2$ concentration stream from a renewable source with carbon oxides and hydrogen from the reforming of natural gas that together balance the electron to carbon atom ratio (e/C) of the substrate entering a reformed gas fermentation zone. This balancing can be achieved without the need for any generation of hydrogen via a water gas shift reaction or other means. Specific embodiments of the process reduce the greenhouse gas impact that methane poses as a starting feed for the production of alcohol by utilizing a source of $CO_2$ that is usually vented to the atmosphere.

First Broad Aspect of the Invention—Reformed Gas Adjustment to Obtain Certain $e^-/C$ It has been found that the efficiency of hydrogen bioconversion in anaerobic processes depends not only on the presence of carbon dioxide in the aqueous fermentation menstruum but also the ratio of electrons to carbon atoms created by use certain off-gas streams from certain types of renewable product production. The processes of this aspect of the invention enable the use of advantageous reformed gas sources and yet obtain enhanced conversion of the reformed gas by adjustment of the composition of the reformed gas by the supply of an additional exogenous gas, preferably a renewable gas, which is primarily CO2. The adjustment in the composition by the addition of at least one other gas is particularly attractive because all hydrogen and carbon oxides values in the feed gases are then available for the bioconversion. Moreover, compositional adjustments can be readily implemented on virtually a real time basis by the blend ratio. Hence, in the event that a unit operation generating reformed gas has an upset or other process change affecting reformed gas composition, the e/C can be adjusted quickly to avoid undue loss of reformed gas values due to the use of less desirable electron to carbon atom ratios.

In this aspect, continuous processes are provided for the anaerobic bioconversion of a gas substrate comprising carbon monoxide, hydrogen and carbon dioxide in contact with an aqueous menstruum containing microorganisms suitable for converting the substrate to alcohol that comprise continuously contacting the gas substrate with the aqueous menstruum to bioconvert the gas substrate to alcohol and providing an alcohol-containing menstruum and a depleted gas phase; continuously withdrawing the depleted gas phase from the aqueous menstruum; continuously or intermittently withdrawing a portion of the menstruum for recovery of the alcohol, the withdrawal being sufficient to maintain the alcohol in the menstruum below a concentration that unduly adversely affects the microorganisms, wherein at least 2 gases having different compositions with one from a renewable source and another from a non-renewable source are used as the gas substrate and may be admixed prior to contact with the aqueous menstruum or separately added to the aqueous menstruum to provide an overall, or cumulative gas substrate having a ratio of electrons to carbon atoms in the range of about 5.2:1 to 6.8:1, preferably between about 5.5:1 to 6.5:1, and most preferably between about 5.7:1 to 6.4:1.

In addition to the use of specific $e^-/C$ ratios is conserving from the methane feed as many available electrons as possible. By the use of a non-oxidative process to produce a reformed gas from natural gas or other non-renewable feeds, this invention can conserve at least 90% and more often 95% or more of the available electrons from the methane in such feeds for use by the microorganisms in the production of alcohol. The minimization of oxygen in the conversion of the methane feed component is an important part of this invention and necessary to minimize or essentially prevent oxidation reactions that wastes electrons and reduces the efficiency of the methane conversion to feed gas for the production of alcohol.

Steam reforming has been found to be a particularly useful type of reforming. Steam reforming typically provides a reformed gas with a high hydrogen content and does not use oxygen so that it provides high conservation of electrons from the methane in the amounts as described above. The high concentration of hydrogen of the steam reformed gas facilitates achieving the desired e/C values in the mixing of the reformed gas with exogenous $CO_2$ from a renewable resource.

In one set of preferred embodiments for this aspect of the invention, reformed gas having a high concentration of hydrogen such as reformed gas generated by steam reforming of methane or coke oven gas can be used with a gas from a process making a renewable product containing a high concentration of carbon oxides, especially a high concentration of carbon dioxide. Autothermal reforming can provide a portion of reformed gas falling within a broad range of electrons to carbon atoms and may be in, above or below the sought ratios. Although a portion of the reformed gas may be provided by autothermal reforming, its use is generally deleterious since its usage of oxygen will reduce the electrons available in the combined gas that goes to the gas to fermentation process.

In some instances, the renewable source of carbon oxides may be relatively inexpensive, especially where carbon dioxide is a substantial portion of the gas, e.g., at least 40 volume percent carbon dioxide. A particularly attractive source of carbon dioxide is from yeast fermentations and in most cases anaerobic yeast fermentations, e.g., fermentations of carbohydrates such as sugars or starches to produce alkanols such as ethanol, propanol, propanediol, butanol and butanediol. Typically the carbon dioxide from these fermentations is a co-product and is relatively free of components that are unduly adverse to microorganisms in the syngas fermentation.

As can be seen, the use of two or more gases enables an alcohol to be produced from both fossil and renewable carbon sources thereby providing an alcohol that has a renewable component. For example, steam reforming of methane provides a reformed gas with a high ratio of hydrogen to carbon oxides. The addition of carbon dioxide from renewable sources can, if desired, result in between about 20 or 30 to 70, preferably 20 to 50, and more preferably 30 to 50, percent of the carbon atoms in the alcohol being from the renewable resource.

The syngas fermentation is conducted in a bioreactor assembly containing one or more bioreactors. Any suitable bioreactor may be used including a continuously stirred bioreactor (CSTR), a bubble column bioreactor (BCBR), a membrane supported bioreactor (MSBR), a moving bed bioreactor (MBBR) any other type of bioreactor that provides a high mass transfer between the substrate and the microorganism contained therein. The bioreactors need not, but can, provide a substantially uniform aqueous menstruum composition.

Second Broad Aspect of the Invention—Alcohol with Renewable Carbon Content

Substantial reserves of natural gas exist, and techniques are being applied to recover natural gas from these reserves. Often, however, these reserves are located remote from large population centers and thus pose transport challenges. Pipelines, which are expensive and time-consuming to construct, can be used to transport large quantities of natural gas. Although natural gas has been shipped via tankers, specialized construction is required and the presence of highly flammable, volatile gas poses safety risks which are heightened in more developed areas. Another fossil fuel having substantial reserves is coal. Many of these reserves are located remote from large population centers and include low rank sources such as subbituminous coal and lignite. Transport of coal is often by rail, and where available, ships and barges. The costs of handling solids for transport are greater than cost for handling liquids. Moreover the coal can contain sulfur, organic nitrogen, and mercury and other metals that pose environmental issues at the location of use as a fuel.

Accordingly, proposals have been made to convert natural gas and coal to liquids that are more capable of being transported with less risk. These proposals include removal of environmentally deleterious components in generating the liquid. Such proposals include converting the fossil fuel to reformed gas and then to a liquid product. One such proposal is the Fischer-Tropsch process that requires substantial capital and operating expense. Recently numerous proposals have been made to bioconvert syngas to alcohol, especially ethanol. Bioconversion of syngas to alcohol has also been proposed for various industrial waste gases such as steel mill gas.

Alcohol has value as a fuel or intermediate for chemical production. Governmental and private interests have placed a premium on sourcing fuels and chemical intermediates from renewable sources. Accordingly, in the United States, a substantial corn ethanol industry has matured, and efforts are being undertaken to generate ethanol from cellulosic sources. The volumes of fuels and chemical intermediates anticipated to be required in the future can result in the deployment of agrarian land to feedstock production in contrast to the production of food. Therefore it is likely that the costs to procure sugar yielding materials and crops may become significantly greater than the cost to procure fossil fuels or industrial waste containing hydrogen and carbon oxides.

Some processes for producing fuels or chemical intermediates from renewable sources generate renewable carbon-containing co-products that are not useful as fuels or chemical intermediates. For instance, yeast fermentations of carbohydrate result in about one molecule of carbon dioxide being generated for each molecule of ethanol produced. Other processes such as the gasification or partial oxidation of renewable carbon feedstocks result in a syngas containing more carbon dioxide than can be converted to fuel or chemical intermediates through anaerobic bioconversion.

Carbon dioxide is also generated from various waste product disposal processes. Sources of renewable carbon, for instance, are incinerated for disposal and result in the generation of carbon dioxide. Renewable carbon-containing waste, such as municipal waste and agricultural waste are subjected to anaerobic biodegradation, e.g., in landfills and anaerobic digesters, to produce biogas which contains methane and carbon dioxide.

Combining, in a bioreactor assembly, reformed gas from a non-renewable carbon source with renewable carbon containing gas results in capture of CO2 that is otherwise released to the atmosphere. Capturing the CO2 and bioconverting at high efficiency produces an alcohol that now has a renewable carbon component. In part, by providing, in a highly cost effective manner, to the bioreactor assembly an overall, or cumulative, gas substrate having an electron to carbon atom ratio between about 5.2:1 to 6.8:1, preferably between about 5.5:1 to 6.5:1, and most preferably between about 5.7:1 to 6.4:1. In most cases the anaerobic bioconversion processes can provide for a high conversion of hydrogen and carbon oxides, e.g., preferably in excess of at least about 85, more preferably in excess of at least about 90 and most preferably in excess of at least 95, mole percent of the hydrogen and carbon oxides. These high conversion efficiencies can be obtained using deep tank or a variety of other bioreactors.

Depending upon the composition of the reformed gas from the non-renewable carbon source and the composition of the renewable carbon-containing gas, an alcohol can be provided that contains between about 20 and 70, say preferably between 20 to 50 and more preferably between, 30 and 50, percent of the carbon from a renewable carbon source. Where the reformed gas from the non-renewable carbon source contains significant amounts of hydrogen, such as coke oven gas and gas from the steam reforming of natural gas, the alcohol typically has a greater renewable carbon content that results in further reducing atmospheric released CO2. Similarly, where the renewable carbon-containing gas contains a high content of carbon dioxide, especially carbon dioxide and methane, the alcohol typically has a greater renewable carbon content. Examples of these renewable carbon-containing gases include, but are not limited to, carbon dioxide from an ethanol plant and biogas, e.g., from a landfill or anaerobic digester. In some of these instances, the greater renewable content of the alcohol has between about 30 and 60 percent of the carbon from renewable carbon.

Third Broad Aspect of the Invention—Integrated Carbohydrate to Alcohol and Anaerobic Reformed Gas Bioconversion Process This aspect of the invention relates to processes for making alcohol from a combination of non-renewable and renewable feed gases. Using carbon dioxide gas from renewable carbohydrate sources is a particularly desirable source of renewable carbon atoms to adjust the electron to carbon atom ratio of a non-renewable reformed gas having a high electron to carbon ratio such as reformed gas from steam reforming of natural gas. The ability to use these non-renewable and renewable feed gas sources results from the discovery that the combination of high conversion and a specific range of e/C ratio provides a surprising productivity to higher alcohols.

In its broadest scope, this aspect of the invention pertains to the use of carbon dioxide gas, which is based upon renewable and non-renewable carbon, to provide a gas substrate for anaerobic bioconversion that has an e/C ratio of between about 5.2:1 to 6.8:1 and preferably 5.7:1 to 6.4:1 and more preferably 5.8:1 to 6.3:1, and sometimes between about 5.8:1 and 6.1:1. In accordance with the more preferred embodiments, additional integrations exist to enhance further the economics of each of these processes.

Thus in this broad aspect of the invention a non-renewable, methane rich gas feed passes to a steam reformer to produce a non-renewable substrate, a portion of which, is continuously introduced into a bioreactor assembly containing an aqueous menstruum and renewable carbon dioxide is introduced into the bioreactor assembly to bioconvert the non-renewable and renewable gas substrate to alcohol and an alcohol-containing menstruum and a depleted gas phase are produced thereby, wherein in the process:

a. the steam reformer produces a gas with and e/C ratio of greater than 7.0:1 and more preferably 7.5:1 with entirely non-renewable carbon content;
   b. gas from the reformer is introduced into a renewable CO2-containing gas to produce a mixed gas with an e/C ratio of 5.7:1 to 6.4 to:1 which is then fed to the aqueous menstruum of the bioreactor assembly;
   c. continuously withdraws depleted gas phase from the aqueous menstruum;
   d. continuously or intermittently withdraws a portion of the menstruum for recovery of the alcohol; and, e. separates the withdrawn portion of the menstruum by distillation to provide alcohol and an aqueous menstruum.

In many instances the renewable CO2-containing gas has an e/C ratio of less than 2.5:1, preferably less than 0.1:1. In some applications of the above described process, the non-renewable and renewable substrates are combined to produce a combined substrate having an e/C in a range of 5.7:1 to 6.4:1 and preferably 5.8:1 to 6.2:1. The reformer is operated primarily with steam and the feed to the reformer preferably consists essentially of methane and steam; the non-renewable substrate and the renewable substrate enter a bioreactor of the bioreactor assembly independently. A portion of the menstruum is withdrawn continuously or intermittently for recovery of the alcohol in a sufficient amount to maintain the alcohol in the menstruum below a concentration that unduly adversely affects the microorganisms.

As stated above, carbon dioxide gas from carbohydrate fermentation sources such as sugar or starch ethanol facilities is a desirable source of renewable carbon atoms to adjust the electron to carbon atom ratio of a reformed gas having a high electron to carbon ratio such as reformed gas from steam reforming This aspect of the invention in its broadest scope pertains to the use of the carbon dioxide gas, which is based upon renewable carbon from corn as a carbohydrate source, to provide a gas substrate for anaerobic bioconversion that has an electron to carbon atom ratio of between about 5.2:1 to 6.8:1.

Thus, the combination of these two substrates provide a desirable e/C with the ability to adjust either the electron or carbon content of the entering gas. As a result this invention avoids any further unit operations, such as the provision of a water gas shift step to change the hydrogen input to the process. Eliminating the need for such a unit operation provides significant cost and operational advantages.

This broad aspect of the invention relates to integrated processes for making alcohol from carbohydrates and gas substrate comprising carbon monoxide, hydrogen and carbon dioxide comprising:
 a. a carbohydrate to alcohol process comprising:
  i. bioconverting under fermentation conditions including the presence of biocatalyst a carbohydrate-containing aqueous broth to provide an alcohol-containing broth which broth contains biocatalyst and carbon dioxide gas;
  ii. removing carbon dioxide gas as a biogas from the alcohol-containing broth;
  iii. separating by distillation alcohol from the alcohol-containing broth and providing a whole stillage containing water, unconverted carbohydrates and biocatalyst;
  iv. separating the whole stillage by centrifugation to provide a thin stillage and distillers grains;
  v. evaporating water from the thin stillage to provide a concentrate containing unconverted carbohydrates, and
 b. a reformed gas to alcohol process comprising:
  i. continuously introducing the gas substrate, a portion of which is from a non-renewable source, into a bioreactor assembly containing the aqueous menstruum to bioconvert gas substrate to alcohol and providing an alcohol-containing menstruum and a depleted gas phase;
  ii. continuously withdrawing depleted gas phase from the aqueous menstruum;
  iii. continuously or intermittently withdrawing a portion of the menstruum for recovery of the alcohol,
  iv. separating the withdrawn portion of the menstruum by distillation to provide alcohol and an aqueous stillage,
 wherein at least a portion of the separated carbon dioxide from step (a)(ii) is used as a portion of the gas substrate in step (b)(i) to provide a gas substrate having an electron to carbon atom ratio of between about 5.2:1 and 6.8:1, preferably between about 5.5:1 to 6.5:1 and most preferably, 5.7:1 to 6.4:1.

Preferably the gas substrate of step (b)(i) comprises reformed gas derived from steam reforming of natural gas or coke oven gas.

This aspect of the invention is particularly advantageous from the standpoint of greenhouse gas generation. Carbohydrate (sugar) fermentation processes produce $CO_2$ as a by-product that is often released in to the atmosphere. In the case of motor fuel production, utilizing by-product CO2 as the renewable source of carbon reduces the greenhouse gas emissions by 50% or more when compared to gasoline. Furthermore, the process of this invention does this in a cost effective manner since by-product CO2 from such carbohydrate fermentation processes is given little value by sugar ethanol producers which makes it a cheap source of $CO_2$. Thus, additional carbon dioxide from carbohydrate fermentation processes is readily available for balancing the overall e/C value of a combined gas substrate that also contains reformed gas generated by reforming.

Additional Operation and Arrangement Modes of the Invention

Another source of carbon values for the anaerobic bioconversion of reformed gas to an alcohol is biogas which contains substantial amounts of both carbon dioxide and methane. Both of the carbon dioxide and the methane are from renewable resources and thus can provide alcohol with a renewable carbon component.

The processes of this aspect of the invention use a combination of steam reforming to provide a reformed gas having a high hydrogen content such that it can be combined with biogas containing a substantial portion of carbon dioxide and yet provide a combined gas in which during anaerobic bioconversion each of hydrogen, carbon monoxide and carbon dioxide are converted to an alcohol such that the depleted gas phase from the anaerobic bioconversion contains a reduced concentration of carbon dioxide. The depleted gas phase can therefore be used in the steam reforming either or both as a fuel to the hotbox of the steam reformer or as a portion of the feed to the steam reformer. In the latter case, because the concentration of carbon dioxide is reduced, an attractive ratio of hydrogen to carbon oxides can be obtained in the produced reformed gas to maximize the amount of biogas that can be incorporated in the feed to the anaerobic bioconversion. It is also possible to separate carbon dioxide from the methane in the depleted gas phase and send the carbon dioxide to the fermenter and a resulting rich methane stream to the hot box.

In some instances, the biogas may contain nutrients for the microorganisms such as sulfur compounds and ammonia or other nitrogen-containing compounds. Additionally, the aqueous menstruum may remove components such as silica, silicates and siloxanes, that could be disadvantageous if the substrate depleted gas phase were to be directly fed to the steam reformer, but which are not unduly adverse to the microorganisms.

This mode of the invention therefore relates to continuous processes for the anaerobic bioconversion of a gas substrate comprising carbon monoxide, hydrogen and carbon dioxide in an aqueous menstruum containing microorganisms suitable for converting the substrate to an alcohol that comprises:

a. steam reforming hydrocarbonaceous feedstock to provide a reformed gas having an electron to carbon ratio greater than about 7:1, preferably greater than about 7.5:1, the steam reforming being performed in a steam reformer having at least one gas reforming section and at least one hotbox section;
b. continuously introducing separately or in admixture into a bioreactor assembly, the reformed gas and biogas, the biogas comprising at least about 20 or preferably at least 25, and sometimes at least 40, mole percent carbon dioxide and preferably at least about 40 mole percent methane, the biogas having an electron to carbon ratio less than about 0.1:1 to provide a cumulative gas substrate having an electron to carbon ratio in the range of about 5.2:1 to 6.8:1, preferably between about 5.7:1 to 6.4:1, and most preferably between about 5.8:1 to 6.3:1;
c. continuously contacting the reformed gas and the biogas with the aqueous menstruum to bioconvert the gas substrate to an alcohol and thereby producing an alcohol-containing menstruum and a substrate depleted gas phase, the contacting being in a bioreactor assembly containing the menstruum, the bioreactor assembly having at least one gas inlet and at least one gas outlet, and at least one bioreactor in the bioreactor assembly is characterized as having a substantially uniform liquid phase and a substantially non-uniform substrate concentration between the gas inlet and the gas outlet portion;
d. continuously withdrawing the substrate depleted gas phase from the aqueous menstruum, the depleted gas phase having a lower mole ratio of carbon dioxide to methane than that of the combined gas;
e. passing at least a portion of the depleted gas phase to the steam reformer of step (a); and
f. continuously or intermittently withdrawing a portion of the menstruum for recovery of the alcohol, the withdrawal being sufficient to maintain the alcohol in the menstruum below a concentration that unduly adversely affects the microorganisms.

Especially where at least a portion of the substrate depleted gas phase is fed to the steam reformer for reformation, the partial pressure of carbon dioxide in the substrate depleted gas phase is less than about 20 or 25 kPa, and most preferably in the range of between about 2.5 or 3.5 and 10 kPa such that the production of hydrogen by the steam reformer is not unduly adversely affected by carbon dioxide reforming to produce carbon monoxide. Often the methane in the substrate depleted off gas is between about 20 to 90, and preferably, 50 to 90, mole percent of the substrate depleted gas phase. The preferred supplemental hydrocarbonaceous feedstock is natural gas.

Preferably the biogas is subjected to ultrafiltration to remove any entrained microorganisms prior to being introduced into the bioreactor assembly. The preferred biogas is an anaerobically derived gas.

This invention can also use a substrate depleted gas phase in the hot box of a steam reformer. In this case hydrogen and carbon oxides in the gas substrate at certain electron to carbon atom ratios are highly converted in an anaerobic bioconversion to alcohol such that the substrate depleted gas phase from the anaerobic bioconversion has sufficient caloric value to offset fuel required for steam reforming to generate reformed gas for use in the gas substrate. The molar concentration of carbon dioxide in the substrate depleted gas phase is below about 20 or 25 percent, and most often in the range of between about 2.5 or 3.5 to 10 percent. A substantial portion of the heating value of the depleted gas phase is from methane and residual hydrogen contained in the gas substrate, at least portion of the methane is provided by breakthrough from the steam reformer. Advantageously, where the gas substrate comprises reformed gas from steam reforming, the nitrogen content of the gas substrate is preferably less than about 10, more preferably less than about 2, mole percent. These lower levels of nitrogen are achievable because steam reforming requires no addition of air or oxygen enriched air to the gas that is being reformed. Since the substrate depleted gas has a high calorific value, the use of unit operations to remove carbon dioxide is not required.

The gas substrate introduced into the bioreactor can have an electron to carbon ratio greater than about 5.2:1, preferably greater than about 5.5:1 and continuously contacts the aqueous menstruum to bioconvert the gas substrate to alcohol and provide an alcohol-containing menstruum and a substrate depleted gas phase. At least an aliquot portion of the substrate depleted gas phase is passed to the hot box section of the steam reformer.

In a preferred for of this arrangement, a bioreactor assembly contains the aqueous menstruum for the anaerobic bioconversion the bioreactor assembly having at least one inlet portion and at least one gas outlet portion and at least one bioreactor in the bioreactor assembly is characterized as having a substantially uniform aqueous menstruum and a substantially non-uniform substrate concentration between the inlet portion and the outlet portion.

In another form of the invention, a bioreactor assembly contains the aqueous menstruum for the anaerobic bioconversion the bioreactor assembly having at least one inlet portion and at least one gas outlet portion. In preferred arrangements at least one bioreactor in the bioreactor assembly is characterized as having a substantially uniform aqueous menstruum and a substantially non-uniform composition of the gas bubbles between the inlet portion and the outlet portion. Without wishing to be limited by theory, it is believed that this type of bioreactor assembly provides for sufficient driving force for hydrogen in gas bubbles to pass into the aqueous fermentation menstruum and thus facilitates obtaining high conversion efficiencies of hydrogen. In some instances, the mole ratio of hydrogen to carbon monoxide in the gas passing to a last bioreactor, or bioreactor stage, is less than about 6.5:1, and if such a source of carbon monoxide is available, less than about 5:1, say, in the range of about 2:1 to 4:1. The preferred processes use a deep tank bioreactor, most preferably a bubble column bioreactor.

Another preferred bioreactor for the bioreactor assembly is a membrane bioreactor. There are various versions of membrane bioreactors. Without limiting the variety of possible membrane arrangements, a preferred membrane bioreactor comprises a plurality of hollow fibers that provide contact of the fermentation liquid, of the microorganism retained by the membrane, and of the substrate gas.

A general arrangement of a membrane bioreactor is disclosed in U.S. patent application Ser. No. 11/972,454 and a particularly preferred arrangement of a membrane bioreactor is disclosed in U.S. Pat. No. 8,329,456. The reference discloses, details of a membrane bioreactor including flow path arrangements, fiber compositions, and sizing. As shown therein the membrane bioreactor can be arranged in many different ways. Of most interest is the function of the membrane with respect to the fermentation liquid, the gas substrate and the microorganisms.

Application Ser. No. 11/972,454, the teachings of which are hereby incorporated by reference, shows an arrangement where the microorganisms are retained as a biofilm on the membrane in direct contact with menstruum. The biofilm may be formed on either side of the membrane. The gas substrate contacts the side of the membrane opposite the biofilm and permeates the membrane to contact the microorganisms that comprise the biofilm. The gas and the biofilm together with the menstruum may be on either side of membrane, but typically the biofilm is on the outside of the membrane to prevent plugging of the fiber lumen.

U.S. Pat. No. 8,329,456, the teachings of which are hereby incorporated by reference, shows a preferred arrangement using an asymmetric membrane that retains the microorganisms in a macropore layer located on the outside of the membrane and in direct contact with the substrate while the fermentation menstruum passes on the side of the membrane opposite the substrate and microorganisms flowing the membrane and in contact with a liquid control layer of the membrane. Permeation of the menstruum through the membrane and into contact with microorganisms in the biopores is controlled by its direct contact with a liquid control layer of the membrane.

The membrane bioreactor will typically contain one or more modules that arrange the hollow fibers. The modules commonly contain a plurality of hollow fibers arranged longitudinally with respect to the length of the fiber and in line with respect to the longitudinal axis of the vessel. The ends of the fibers are most often retained in a potting material of resin that exposes open end of the fiber for fluid flow there through. Each section of potted fibers forms a separate module.

Series flow of both gas and menstruum through individual membrane bioreactors is shown in both the application and the patent. U.S. Pat. No. 8,101,387, the teachings of which are hereby incorporated by reference, also shows a method for sequencing bioreactors in serial flow. Both patents and the application show arrangements for adjusting gas flow between the bioreactors. These references also show the typical construction of the membranes into elongated modules with the hollow fibers extending along the length of modules. The substrate then enters and leaves the modules through gas distribution and gas collection chambers that communicate with the inlets and outlets of the hollow fiber lumens.

In the present invention a plurality of membrane bioreactors are used in serial gas and liquid flow from bioreactor to bioreactor. As the menstruum passes through the series of bioreactors the alcohol concentration will typically increase and reach the highest concentration in the last bioreactor. Thus, uniformity of alcohol concentration does not exist from bioreactor to bioreactor. In addition without any adjustment of the gas between bioreactors, the e/C ratio will vary through the series of bioreactors.

An essentially uniform e/C may be maintained for the assembly. Additional substrate gas or portions thereof are readily added between bioreactors or modules in the overall assembly. Furthermore, the number of additions is readily varied by adjusting the size of the modules, primarily increasing the length or the number of fibers in the modules, to increase the gas addition points between the individual membrane modules. Thus, composition gas substrate may be adjusted as desired by the addition or withdrawal of gas between the number of modules or bioreactors that are provided. The desired e/C values are in the range of about 5.2:1 to 6.8:1, preferably between about 5.5:1 to 6.5:1, and most preferably between about 5.7:1 to 6.4:1. The substrate gas, also be adjusted to keep its carbon monoxide concentration below that which unduly inhibits the productivity of the microorganisms.

Without some adjustment in its composition, the menstruum of the last bioreactor in the series will have the highest alcohol titer. The assembly may be able to operate with its highest alcohol titer in the last module of the bioreactor assembly in the liquid flow sequence of bioreactors. However, if desired the alcohol concentration may be reduced across intermediate stages of the serial bioreactors or modules by withdrawal of relatively higher alcohol menstruum and/or the addition of fresh menstruum between serial bioreactor stages and/or modules in the bioreactor assembly. Typically the alcohol will be kept below a level that unduly adversely affects the microorganism and usually below a concentration of 25 grams per liter. Thus, the membrane bioreactor offers a great deal of flexibility for controlling the e/C ratio and the alcohol concentration as the substrate and menstruum pass serially through the bioreactor assembly. Furthermore, the assembly of membrane bioreactor modules and staging the contacting the modules provides and overall gas conversion of greater than 90%. (See U.S. Pat. No. 8,101, 387 issued Jul. 17, 2012.)

Preferably the gas substrate being introduced into the bioreactor assembly comprises at least about 90, preferably at least about 95, mole percent of carbon monoxide, hydrogen and carbon dioxide.

DETAILED DISCUSSION

Definitions

Figure 1:
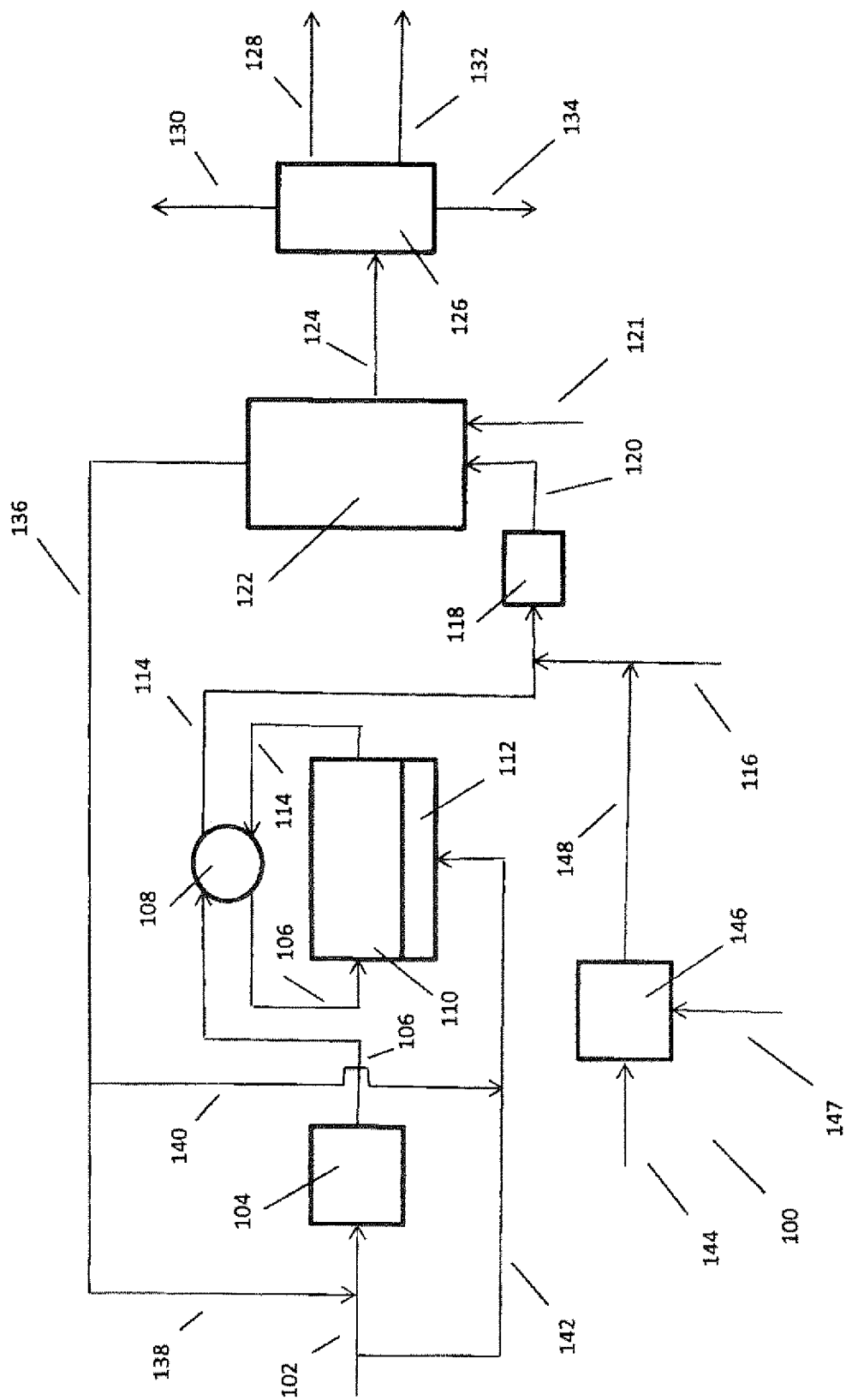
FIG. 1 is a schematic depiction of an apparatus suitable for practicing certain broad aspects of the processes of this invention.

As used herein, the following terms have the meanings set forth below unless otherwise stated or clear from the context of their use.

The use of the terms "a" and "an" is intended to include one or more of the element described.

Alcohol means one or more alkanols containing two to six carbon atoms. In some instances the alcohol is a mixture of alkanols produced by the microorganisms contained in the aqueous menstruum.

Biogas means a gas produced from a renewable source of carbon and preferably containing at least about 20 mole percent carbon dioxide.

Anaerobically derived gas means biogas produced by the anaerobic digestion or fermentation of organic matter in the absence of oxygen and primarily contains methane and carbon dioxide.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switch grass, corn (including corn stover), hemp, sorghum, sugarcane (including bagas), and the like; and waste such as garbage and municipal waste. Biomass does not include fossil fuels such as coal, natural gas, and petroleum.

The term Component Composition means the composition of a gas where both water and nitrogen have been excluded from the calculation of the concentration of the components. As used herein, unless otherwise stated, compositions of gases are on an anhydrous basis and exclude the presence of nitrogen.

Electron to carbon ratio is calculated as the quotient of the quantity of two times the sum of the concentrations of carbon monoxide and hydrogen divided by quantity of the sum of the concentrations of carbon monoxide and carbon dioxide:

$$e^-/C=2([CO]+[H_2])/([CO]+[CO_2]).$$

The abbreviation ppm means parts per million. Unless otherwise stated or clear from the context, ppm is on a mole basis (ppm (mole)).

Aqueous menstruum, or aqueous fermentation menstruum, means a liquid water phase which may contain dissolved compounds including, but not limited to hydrogen, carbon monoxide, and carbon dioxide.

Intermittently means from time to time and may be at regular or irregular time intervals.

A concentration of the alcohol below that unduly adversely affects the rate of growth of the culture of microorganisms will depend upon the type of microorganism and the alcohol. An unduly adverse effect on the growth rate means that a significant, usually at least a 20 percent, decrease in the growth rate of the microorganisms is observed in comparison to the growth rate observed in an aqueous menstruum having about 10 grams per liter alcohol therein, all other parameters being substantially the same.

Substantial uniformity in liquid phase means that composition of the liquid phase is substantially the same throughout a bioreactor. Usually the concentration of the alcohol is within about 0.2 mole percentage points in a uniform liquid phase.

Substantial non-uniformity in the gas phase means that the concentration (both in the gas bubbles and dissolved) of at least one component provided by the gas substrate changes by at least 50 percent between the point of entry of the gas into a bioreactor and the point that the gas emerges from the aqueous fermentation menstruum.

Deep tank bioreactor is a bioreactor having a depth of at least about 10 meters and can be operated to provide a substantial non-uniform substrate composition over the depth of the aqueous menstruum contained in the bioreactor. The term bubble column bioreactor as used herein refers to a deep tank bubble column bioreactor unless otherwise explicitly stated and include deep tank reactors where the gas is introduced as small bubbles to promote mixing. A commercial scale bioreactor has a capacity for aqueous menstruum of at least 1 million, and more preferably at least about 5, say, about 5 to 25 million, liters.

Stable gas-in-liquid dispersion means a mixture of gas bubbles in liquid where the bubbles predominantly flow in the same direction as the liquid currents in the bioreactor and may cause currents in the bioreactor, and the dispersion is sufficiently stable that it exists throughout the aqueous menstruum.

Reformed gas means a gas containing at least one of hydrogen and carbon monoxide and may, and usually does, contain carbon dioxide.

Coal gas has a typical composition of between about 3 and 8 volume percent carbon dioxide, about 20 to 35 volume percent carbon monoxide, about 12 to 25 volume percent hydrogen, and essentially the balance comprising nitrogen.

Coke oven gas has a typical composition of between about 1 and 5 volume percent carbon dioxide, about 3 and 10 volume percent carbon monoxide, about 20 and 40 volume percent methane, about 40 and 60 volume percent hydrogen with the balance being primarily nitrogen.

Anaerobic digester gas has a typical composition of between about 25 and 50 volume percent carbon dioxide and about 40 and 70 volume percent methane with small amounts of hydrogen, hydrogen sulfide, ammonia, and nitrogen.

Landfill gas has the typical composition of between about 35 and 60 volume percent carbon dioxide and about 35 and 60 volume percent methane with small amounts of carbon monoxide, hydrogen, hydrogen sulfide, oxygen, and nitrogen.

Steel mill gas has a composition of between about 30 and 85 volume percent carbon monoxide, about 10 to 40 volume percent carbon dioxide, and about 0 to 15 volume percent hydrogen. Nitrogen is generally present and may constitute up to about 30 volume percent of the steel mill gas. Other minor components are typically present.

Non-renewable gas stream means a gas derived from natural resources that takes at least a geologic age to replace once depleted and for this invention refers primarily to natural gas or methane derived from fossil fuels.

Renewable sources or renewable carbon means a source of carbon that can be replaced in less than a millennium and in most cases in several years or less.

Natural gas means a combustible mixture of gaseous hydrocarbons from sedimentary rocks usually containing over 75% methane with minor amounts of 2-4 carbon alkanes.

Overview

The processes of this invention provides utilization of CO2 from renewable sources that provides high anaerobic bioconversion efficiencies of combined gas substrates to alcohol. Various aspects of the invention use certain electron to carbon ratios. And various aspects of the invention facilitate achieving a high conversion of a combined gas substrate with the alcohol having a renewable carbon component.

Reformed Gas Generation

The source of the reformed gas is not critical to a number of the broad aspects of this invention although the use of reformed gas derived from steam reforming is particularly attractive. Gasification, partial oxidation, and reforming (principally steam but supplemented with autothermal in some cases) of biomass or fossil carbonaceous materials are representative processes for generating reformed gas. Gasification and partial oxidation processes are disclosed in copending U.S. patent application Ser. No. 13/304,902, filed on Nov. 28, 2011, hereby incorporated by reference in its entirety. Steam reforming is a widely practiced commercial unit operation. See Logdberg, et al., "Natural Gas Conversion", Haldor Topsoe publication (undated). Rice, et al, in "Autothermal Reforming of Natural Gas to Synthesis Gas", Reference: KBR Paper #2031, Sandia National Laboratories, April 2007, discuss autothermal reforming and conditions. Reforming in the presence of carbon dioxide is known as carbon dioxide reforming with the partial pressure of carbon dioxide causing a shift in the product distribution of the reforming. See, for instance, Madsen, et al, "Industrial Aspects of $CO_2$-reforming", Paper No. 28f, presented at the AIChE Spring Meeting, Houston, Tex., March 1997. Reforming is a temperature dependent equilibrium reaction, and thus the addition of hydrogen, carbon monoxide or carbon dioxide will affect the distribution of steam, hydrogen, carbon monoxide and carbon dioxide from the fresh feed although the distribution in the produced reformed gas will be set by the thermodynamic equilibria.

This invention depends on having a high ratio of hydrogen to CO2 available, thus, steam reforming is at least partially and more typically exclusively employed due to the high hydrogen concentration of the produced reformed gas and the relative absence of contaminants that must be removed to prevent deleterious effects on the microorganisms for the anaerobic bioconversion reformed gas to alcohol. Additionally, steam reforming is non-oxidative process; thus, it provides a reformed gas that is relatively free of nitrogen which would be present in the reformed gas produced by a partial oxidation or autothermal reforming process that uses air or enriched air as the oxygen source. Another advantage of steam reforming is that the depleted gas phase from the bioreactors can be used as a portion of the fuel required for providing the heat for the steam reforming. By using the depleted gas phase to provide heat, an offset of fresh carbonaceous feed occurs and thereby enhances the net conversion of fresh carbonaceous feed to alcohol. The portion of the carbonaceous feed that can be offset will depend upon the volume and heating value of the depleted gas phase. Where this option is employed, frequently about 10 to 50 mass percent of the carbonaceous feed used for fuel in the hotbox of the steam reformer can be offset.

Since the unit operations to make the reformed gas can vary widely, it is understood that the compositions of the combined gas substrate may similarly vary widely including the presence of components other than hydrogen, carbon monoxide and carbon dioxide, which components may be inert such as nitrogen and methane or components that may have to be removed due to potential adverse effects on the microorganisms such as hydrogen cyanide. Processes for removing adverse components include those disclosed in U.S. patent application Ser. No. 13/304,902, filed on Nov. 28, 2011; Ser. No. 13/440,953, filed on Apr. 5, 2012; and Ser. No. 13/525,079, filed on Jun. 15, 2012; U.S. Pat. No. 7,927,513 filed on Oct. 27, 2009; and U.S. Pat. No. 8,303,849, filed on Nov. 9, 2010, all hereby incorporated by reference in their entireties. Also, the relative ratios among hydrogen, carbon monoxide and carbon dioxide may vary widely. An advantage of the processes of this invention is that such variations in the relative ratios of the gas coming from the non-renewable source can be accommodated by the renewable source to provide a substrate gas to the bioreactor assembly that enables achieving a high conversion of hydrogen and carbon monoxide to alcohol.

In some instances, it may be desired to use more than one source of reformed gas, and it may be desired to use different types unit operations, e.g., a steam reformer and an autothermal reformer or partial oxidation unit or gasifier, to produce reformed gas so as to provide the desired substrate gas composition. However, the deleterious effect of the oxygen on obtaining the desired high recovery of electrons from the methane in the feed will again lead away from any use of oxidative reforming.

The Aspects of the Invention Using Reformed Gas Adjustment

In certain of the broad aspects of the processes of this invention, the combined gas composition is adjusted to provide one or more of certain electron to carbon ratios and renewable carbon in the alcohol product. Adjustment is effected by the addition of one or more of these components from another source having a different composition. As noted above, the use of two different combined gas substrate producing unit operations may be used to provide a composite combined gas substrate having the sought composition. Alternatively, a hydrogen or carbon oxides-containing gas from another process can be used for the adjustment along with the CO2 from renewable sources.

The invention focuses on using a gas containing a high concentration of hydrogen is available, such as reformed gas from steam reforming, in combination with a renewable component to make the alcohol product. The carbon dioxide added from the renewable resource to meet the electron to carbon atom parameter desired for high conversion of hydrogen and carbon monoxide can also be directly or indirectly from biomass.

In this invention the main source of relatively high purity carbon dioxide is from ethanol plants bioconverting carbohydrates to ethanol or other alkanols and diols. In some instances, between about 20 to 45 or more percent of the oxygenated organic product can be composed of carbon from renewable sources where using a methane steam reforming unit operation to produce combined gas substrate.

Another source of carbon dioxide-containing gas that can be used to adjust the composition of the combined gas substrate is biogas such as from anaerobic digestion processes and from landfills. An advantage of the biogas is that it contains a significant amount of methane which can be used as, for instance, feedstock for a steam reforming unit operation or fuel within the process, e.g., for generating heat for distillation of the alcohol from the aqueous menstruum or for the hotbox of a steam reformer. Where the depleted gas phase from the bioreactor assembly is used as a feed for the steam reformer, up to about 70 percent of the oxygenated organic product can be composed of carbon from renewable sources.

The carbon monoxide-containing gas may be introduced into the aqueous menstruum in any suitable manner.

Table I provides typical compositions of the cumulative substrate gas fed to the bioreactor assembly using reformed gas from steam reforming.

TABLE I

| Component | Minimum | Maximum | Preferred Minimum | Preferred Maximum |
|---|---|---|---|---|
| Carbon Monoxide, mole % | 0 | 30 | 10 | 20 |
| Hydrogen, mole % | 30 | 75 | 50 | 70 |
| Carbon Dioxide, mole % | 2.5 | 50 | 10 | 15 |
| Methane, mole % | 0.1 | 30 | 0.3 | 10 |
| Nitrogen, mole % | 0 | 10 | 0 | 5 |
| Hydrogen cyanide, ppm(mole) | 0.001 | 2 | 0.001 | 0.3 |
| Other, ppm(mole) | 20 | 10000 | 20 | 10000 |

(Excluding water)

Alcohol, Microorganisms and Fermentation Conditions:

The alcohol or alcohols produced in the processes of this invention will depend upon the microorganism used for the fermentation and the conditions of the fermentation. One or more microorganisms may be used in the fermentation menstruum to produce the sought alcohol. Bioconversions of CO and $H_2/CO_2$ to propanol, butanol, ethanol and other alcohols are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the combined gas substrate components: CO, $H_2$, $CO_2$ individually or in combination with each other or with other components that are typically present in reformed gas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment a combined gas substrate to ethanol and/or n-butanol. *Clostridium ragsdalei* may be used, for example, to ferment a combined gas substrate to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 U.S. Pat. No. 8,143,037, filed on Mar. 19, 2010. All of these references are incorporated herein in their entirety.

Suitable microorganisms for bioconversion of a combined gas substrate to alcohol generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. U.S. Pat. No. 7,704,723, hereby incorporated by reference in its entirety, discloses the conditions and contents of suitable aqueous menstruum for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous menstruum composition, and combined gas substrate residence time, are preferably sufficient to achieve the sought conversion efficiency of hydrogen and carbon monoxide and will vary depending upon the design of the fermentation bioreactor and its operation. The pressure may be sub-atmospheric, atmospheric or super atmospheric, and is usually in the range of from about 90 to 1000 KPa absolute and in some instances higher pressures may be desirable for biofilm fermentation bioreactors. As most bioreactor designs, especially for commercial scale operations, provide for a significant height of aqueous menstruum for the fermentation, the pressure will vary within the fermentation bioreactor based upon the static head.

The fermentation conditions are preferably sufficient to effect conversion of at least about 85, preferably at least about 90, percent of the hydrogen in the substrate gas fed to the bioreactor assembly to alcohol. As stated above, in the case of a bubble column bioreactor a combination of bubble size and duration of contact with the aqueous fermentation menstruum are necessary to achieve these high conversions. However, the ease and ability to achieve these high conversions is also dependent upon having the specified electron to carbon ratios and carbon dioxide partial pressures in the substrate depleted gas phase. For commercial operations, the fermentation operation preferably provides a total molar conversion of hydrogen and carbon monoxide in the substrate gas feed in the range of at least about 93, preferably at least about 97, mole percent. If required to provide adequate contact time between the gas bubbles and the aqueous fermentation menstruum, more than one bioreactor may be used in gas flow series in the bioreactor assembly. The use of sequential deep bubble column bioreactors is disclosed in U.S. patent application Ser. No. 13/243,062, filed on Sep. 23, 2011, herein incorporated by reference in its entirety.

The rate of supply of the gas feed under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important.

Preferably, for a suspended type cell type of fermentation zone where microorganisms float in aqueous menstruum, the substrate gas is introduced into the bioreactor in the form of microbubbles. Often the microbubbles have diameters in the range of 0.01 to 0.5, preferably 0.02 to 0.3 millimeter. Preferably the substrate gas is added to the suspension of microorganisms by injection using a motive fluid. Variations in the motive liquid flow rate can be used to modulate the microbubble size and thus modulate the rate of transfer of carbon monoxide and hydrogen to the liquid phase. Moreover, the modulation provides microbubbles that provide a stable gas-in-liquid dispersion. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The bubble size generated by the injectors will be influenced by, among other factors, the rate of liquid flow through the injector and the ratio of gas phase to liquid phase passing through the injector as well as characteristics of the aqueous menstruum itself including, but not limited to its static liquid depth. See also, U.S. patent application Ser. No. 13/243,062, filed on Sep. 23, 2011. In some instances the microbubbles which form a less dense gas-liquid dispersion and any motive fluid used to generate the microbubbles, can facilitate liquid mixing in a bioreactor.

Bioreactor Assembly

The bioreactor assembly may comprise one or more bioreactors which may be, with respect to gas flow, in parallel or in series flow. The bioreactor assembly preferably contains a bioreactor that is characterized as having a substantially uniform aqueous phase composition and a substantially non-uniform substrate concentration. Representative types of these bioreactors include commercial scale, bubble column bioreactors, stirred tank and bioreactors having gas-lift riser(s) of the type discussed above as well as other types of bioreactors including stirred tank bioreactors; trickle bed bioreactors; biofilm bioreactors; moving bed bioreactors; membrane bioreactors and static mixer bioreactors including, but not limited to, pipe bioreactors. A plurality of bioreactors in sequential gas flow may be desired where the substrate concentration in a bioreactor tends to be relatively uniform. Where more than one bioreactor is used in gas flow series, at least the terminal bioreactor in the series has this characterization. Representative of these types of bioreactors include commercial scale, bubble column bioreactors, stirred tank and bioreactors having gas-lift riser(s) of the type discussed above as well as other types of bioreactors including stirred tank bioreactors; trickle bed bioreactors; biofilm bioreactors; moving bed bioreactors; membrane bioreactors and static mixer bioreactors including, but not limited to, pipe bioreactors. A plurality of bioreactors in sequential gas flow may be desired where the substrate concentration in a bioreactor tends to be relatively uniform.

Because of economy of capital cost and operation, deep tank bioreactors are preferred. The deep tank bioreactors, in order to provide the sought contact time with the bubbles have a depth of at least 10 meters with stirred tank bioreactors often requiring less of a depth since the stirring can cause the bubbles to remain in the aqueous menstruum for a greater duration of time than those in a bubble column bioreactor. Regardless of the type of deep tank bioreactor, especially where using microbubbles that promote a stable dispersion of bubbles in the aqueous menstruum, mixing currents exist that not only assure the relatively uniform aqueous phase composition but also increase the contact time between the gas bubbles and the aqueous menstruum.

The processes of this invention are particularly attractive for deep tank bubble column bioreactors which are less expensive from cost and operating standpoints than other types of deep tank bioreactors. Where bubble column bioreactors are used, the depth of the aqueous fermentation menstruum is often at least about 15, say, between about 20 and 30, preferably between about 20 and 25, meters. The significant depths can be used in the bubble column as the substrate gas compositions provide a relatively low partial pressure of carbon monoxide even with these significant depths of aqueous fermentation menstruum. Where more than one bioreactor is used in gas flow series, the initial bioreactor may be of any suitable.

One broad aspect of the processes of this invention involve the use of at least two bioreactors, or bioreactor stages, in gas flow sequence where at least the last bioreactor stage has a substantially uniform liquid composition and a substantially non-uniform substrate composition. In this aspect of the processes of the invention, carbon monoxide is introduced to adjust the mole ratio of hydrogen to carbon monoxide and provide a hydrogen to carbon atom ratio in that bioreactor stage in the range of about 5.2:1 to 6.8. Preferably the mole ratio of hydrogen to carbon monoxide in the introduced carbon monoxide is less than about 5:1, say, in the range of about 2:1 to 4:1. While not wishing to be limited to theory, it is believed that the bioconversion of carbon monoxide which results in the formation of carbon dioxide, provides localized environments favoring the bioconversion of hydrogen to alcohol.

Any suitable method may establish contact between the carbon monoxide containing gas and the fermentation menstruum. For instance, if the bioreactor stage is a separate bioreactor vessel, the carbon monoxide-containing gas may be admixed with the gases passing to the bioreactor vessel. If the bioreactor stage is a zone with in a single bioreactor vessel, the carbon monoxide-containing gas may be introduced by sparging, liquid injection, or the like into that zone. Where using a bubble column bioreactor, the region at which the carbon monoxide-gas is preferably introduced will be in an upper portion of the bioreactor which has a reduced static head. Thus, carbon monoxide-containing gas can have a relatively high carbon monoxide concentration.

Another type of bioreactor suitable for the practice of this broad aspect of the invention uses a jet loop in at least the last bioreactor stage wherein the carbon monoxide-containing gas is used as a motive fluid for the gas lift.

Substrate Depleted Gas Phase

The depleted gas phase egressing from the aqueous fermentation menstruum will contain a small fraction of the hydrogen and carbon oxides introduced into the bioreactor assembly as the substrate gas. Inerts, such as nitrogen and primarily methane, will comprise a significant portion of the depleted gas phase. Thus the depleted gas phase has significant heating value when combusted or can be recycled, at least in part, to the unit operation used for producing the reformed gas. The carbon dioxide content of the depleted gas phase is sufficiently low that a recycle to the unit operation used for producing the reformed gas has a relatively immaterial effect on the reformed gas generation. The depleted gas phase may also contain sulfur-containing compounds, alcohol and the like volatilized from the aqueous fermentation menstruum. Table II provides typical concentrations of the major components in the substrate depleted gas phase from the bioreactor assembly using reformed gas from a steam reformer The ratio of methane to hydrogen varies depending upon the amount of methane in the combined gas substrate, the conversion of hydrogen and whether a methane-containing carbon dioxide gas is used to adjust the electron to carbon ratio.

TABLE II

| Component | Usual, mole percent at 100 kPa absolute | Preferred, mole percent at 100 kPa absolute |
| --- | --- | --- |
| Carbon monoxide | 0 to 5 | 0 to 1.5 |
| Nitrogen | 0 to 10 | 0 to 2 |
| Methane | 5 to 90 | 5 to 80 |
| Carbon dioxide | 2.5 to 40 or 2.5 to 30 | 3.5 to 30 or 3.5 to 10 |

(Mole percentages on an anhydrous basis, partial pressure include water vapor. The gas feed may contain other components)

Product Recovery:

The fermentation vessel may have added from time to time or continuously one or more streams of water, nutrients or adjuvants, and microorganisms. A portion of the aqueous menstruum is withdrawn from time to time or continuously from the bioreactor for product recovery. Usually, the withdrawal is made at a point at the upper portion of the aqueous menstruum in the vessel. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679, herein incorporated by reference in its entirety, shows an arrangement for a product recovery bioreactor that recovers an ethanol product from a bioreactor.

Drawings

A general understanding of the invention and its application may be facilitated by reference to the Figures. The Figures are not in limitation of the broad aspects of the invention.

FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other alcohols such as i-butanol, n-butanol, and n-propanol.

Natural gas is used for providing the reformed gas for use in apparatus 100. It should be recognized that other carbonaceous sources can be used to provide reformed gas. Natural gas is supplied via line 102 and passed to pretreatment assembly 104. Pretreatment assembly 104 typically is adapted to remove sulfur compounds from the natural gas. In some instances, pretreatment assembly 104 is encompassed within a steam reforming unit operation.

The natural gas having its sulfur content reduced is passed via line 106 to heat exchanger 108 and then to steam reformer 110. Steam reformer 110 converts the hydrocarbons in the natural gas to a reformed gas containing hydrogen, carbon monoxide and carbon dioxide. Lower pressure operations of steam reformer 110 provide less methane breakthrough than at higher pressure operations. Accordingly, for purposes of discussion, a lower pressure steam reforming unit operation is used, and the reformed gas contains about 75 mole percent hydrogen, about 18 mole percent carbon monoxide, about 5.5 mole percent carbon dioxide, and about 1.5 mole percent methane on an anhydrous basis.

The steam reforming is endothermic and hotbox 112 is provided to supply heat for the steam reforming. Reformed gas exits steam reformer 110 via line 114 which directs the reformed gas to heat exchanger 108 to preheat the incoming natural gas to steam reformer 110. After passing through heat exchanger 108, carbon dioxide is supplied to the reformed gas in line 114 via line 116 in an amount sufficient to adjust the electron to carbon ratio of the combined gas substrate to about 6.1:1 and provide the sought amount of carbon dioxide in the depleted gas phase (off gas) from the bioreactor assembly. As shown, the combined gas substrate and carbon dioxide stream is subjected to treatment in combined gas substrate purification unit 118. The function of combined gas substrate purification unit 118 will depend upon the source of the reformed gas and carbon dioxide and serves to remove components that may be adverse to the microorganisms used for the anaerobic fermentation of the combined gas substrate to ethanol such as hydrogen cyanide, oxygen, ethylene, and acetylene. Combined gas substrate purification unit 118 is optional, and thus using reformed gas from a steam reformer and carbon dioxide from an ethanol plant, it is not essential for the process depicted in FIG. 1. It has also been found that the application of this invention to making alcohol using a renewable CO2 source that has been found to be clean, i.e. carbon dioxide from corn alcohol production, will not need any purification before it is used.

The combined gas substrate and carbon dioxide stream (substrate gas) is passed from combined gas substrate purification unit 118 to bioreactor assembly 122 via line 120. Bioreactor assembly 122 comprises a plurality of deep tank bubble column bioreactors, one of which is shown in the drawing. Each deep tank bioreactor contains an aqueous fermentation menstruum having a depth of about 20 meters. The substrate gas is introduced at the bottom of the bioreactor in the form of finely dispersed microbubbles, e.g., using a slot eductor. The duration of the microbubbles in the bioreactor is sufficient to bioconvert at least 90 percent of the hydrogen and at least 98 percent of the carbon monoxide to ethanol.

Aqueous fermentation menstruum is continuously withdrawn from bioreactor assembly 122 via line 124. The withdrawn fluid is passed to a product recovery assembly generally designated by 126. Product recovery assembly 126 comprises a number of unit operations to remove solids, entrained gases and recover ethanol. Usually product recovery assembly 126 contains a distillation assembly to fractionate the withdrawn fluid into an ethanol product stream which is removed via line 128 and a water fraction which is removed via line 132. Centrifuges or other solid-liquid separation unit operations may be used to remove cells and other solid debris from the fluid prior to it being passed to the distillation assembly, or the fluid may be passed to the distillation assembly without the removal of solids with the solids being removed with the still bottoms. As shown, a solids-containing stream is removed from product recovery assembly 126 via line 134. The solids-containing stream may be directed to digesters to recover carbon and nutrient values. The withdrawn fluid will also typically include lower boiling components such as methane and hydrogen. These lower boiling components are shown as being removed from a product recovery assembly 126 via line 130. Due to the high efficiency of the processes of this invention, often the lower boiling components have a lower heating value and are sent to a flare for disposal.

Returning to bioreactor assembly 122, make-up water to replenish aqueous menstruum removed for product recovery is replaced directly into bioreactor 122 or at any convenient input location. The make-up water may contain nutrients and other adjuvants for the anaerobic fermentation, and may also contain microorganisms for the bioconversion. Substrate depleted gas phase is emitted from the top of the aqueous fermentation menstruum in the bubble column bioreactor. The depleted gas phase contains about 3 volume percent carbon dioxide at substantially atmospheric pressure. The depleted gas phase is withdrawn from bioreactor assembly 122 via line 136. The depleted gas phase contains methane, hydrogen, carbon dioxide, and relatively little carbon monoxide and thus has value either as a supplement to the natural gas forced steam reforming or as a fuel for the steam reformer. As shown, the depleted gas phase in line 136 can be passed via line 138 to line 102 and then passed to pretreatment assembly 104. Since the depleted gas phase is derived from contact with the aqueous fermentation menstruum, it can contain sulfur compounds that were present in the aqueous menstruum as adjuvants for the microorganisms. The pretreatment assembly 104 serves to remove these sulfur compounds to provide a gas feed suitable for the catalytic steam reforming. In addition, or alternatively, depleted gas phase may be passed via line 140 to line 142 to supply natural gas to hotbox 112 for steam reformer 110. As shown, line 142 obtains the natural gas for hotbox 112 from line 102.

Carbon dioxide to provide the desired electron to carbon ratio for the substrate gas is obtained from an ethanol plant as described above. Other sources of carbon dioxide can be used. FIG. 1 illustrates that a carbonaceous material can be passed via line 144 to gasification unit 146. Gasification unit 146 serves to gasify the carbonaceous material, e.g., wood, to generate a gas containing carbon dioxide, carbon monoxide and hydrogen. Considerable flexibility exists in the operation of gasification unit 146 to provide a desired mole ratio of carbon dioxide to hydrogen such that when combined with the reformed gas from steam reformer 110, the substrate gas has the desired electron to carbon ratio and carbon dioxide content. Reformed gas exits gasification unit 146 via line 148. Not shown, but often desirable, is using the reformed gas which is at a high temperature as a source of heat for indirect heat exchange with the natural gas being provided to steam reformer 110. The reformed gas is directed to line 116 where it is combined with the reformed gas from steam reformer 110 in line 114. Combined gas substrate purification unit 118 is typically used. Combined gases can contain aromatic, ethylenic, acetylenic and hydrogen cyanide components that are preferably substantially removed prior to introducing the substrate gas into bioreactor assembly 122.

In another embodiment illustrated by FIG. 1, a portion of the feedstock in line 102 may be passed via lines 142 and 144 to an autothermal reformer 146. Line 147 provides the oxygen for the autothermal reforming. The oxygen may be sourced from an oxygen plant and thus be relatively high purity, from air or from oxygen enriched air produced by admixing air with purer forms of oxygen or by partial separation of nitrogen from air, e.g., by membrane separation or swing sorption. In this embodiment, the reformed gas may have a suitable electron to carbon atom ratio for introducing into bioreactor assembly 122 after suitable removal of deleterious components.

Figure 2:
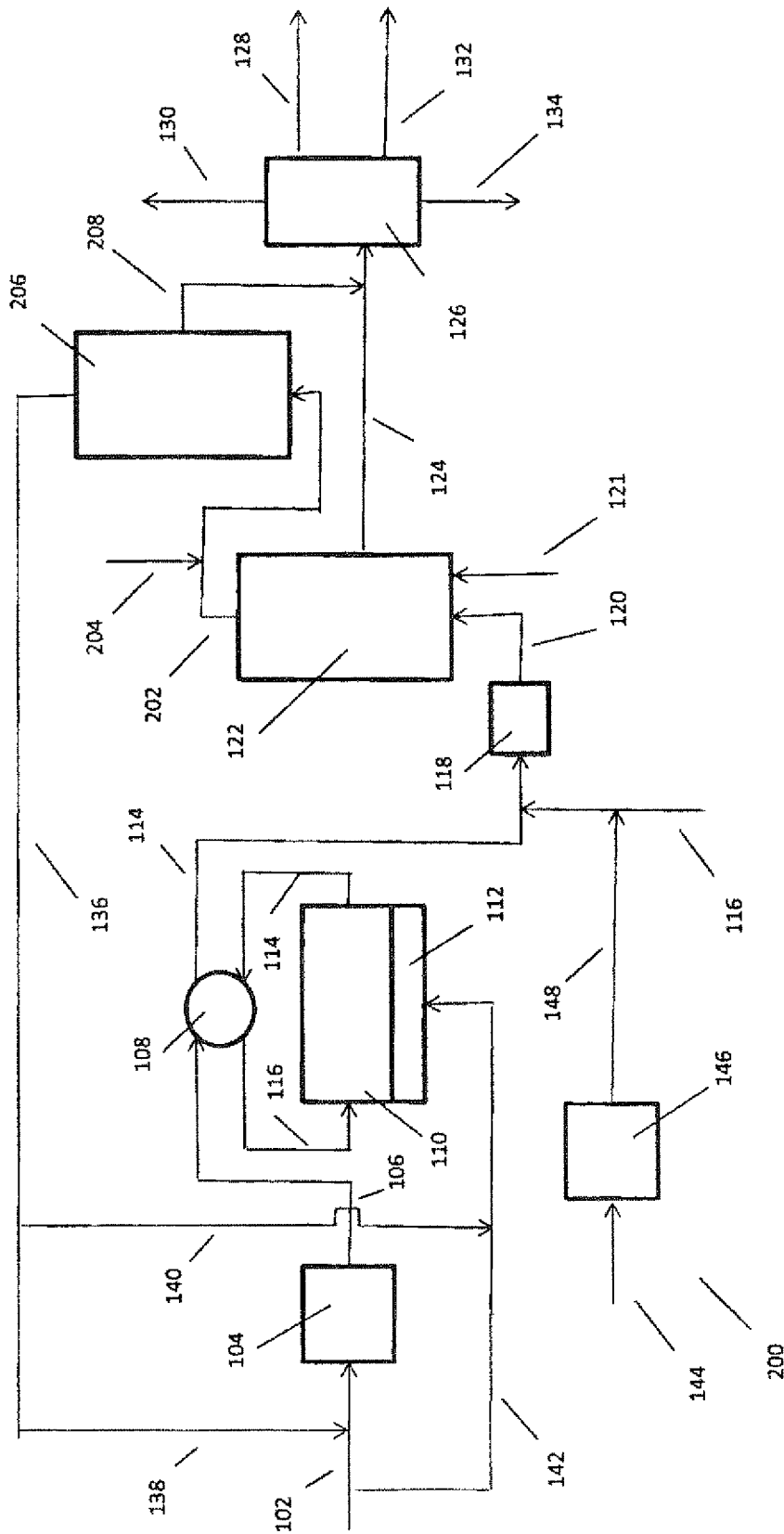
FIG. 2 is a schematic depiction of another apparatus suitable for practicing certain broad aspects of the processes of this invention.

FIG. 2 is a schematic depiction of apparatus 200 using two bioreactors in gas flow series suitable for obtaining high conversion efficiencies of hydrogen and carbon oxides to ethanol. The same numerals used in the description of the apparatus of FIG. 1 are used with respect to this FIG. 2 and the same description applies except as set forth below.

In bioreactor 122 a major portion of the hydrogen and virtually all, say, 90 or 95 percent or more, of the carbon monoxide are converted to ethanol, and an off gas containing hydrogen, carbon dioxide and relatively little carbon monoxide is generated. The off gas has an electron to carbon atom ratio greater than about 7:1. The off gas is withdrawn from bioreactor 122 via line 202 and passed to bioreactor 206 which is in gas flow sequence to bioreactor 122. Prior to the off gas entering bioreactor 206, carbon monoxide-containing gas supplied by line 204 is admixed with the off gas to provide a combined gas having a hydrogen to carbon atom ratio between about 5.5:1 to 6.5:1 and a hydrogen to carbon monoxide ratio of less than about 0.2:1. The carbon monoxide-containing gas may be a coal gas or other suitable gas, and may contain hydrogen and carbon dioxide such as reformed gas generated by gasification unit 146.

Bioreactor 206 converts hydrogen and carbon oxides to ethanol. Bioreactor 206 is a bubble column bioreactor with the combined off gas from bioreactor 122 and the carbon monoxide-containing gas being introduced in the form of finely divided bubbles. Aqueous menstruum containing ethanol is withdrawn from bioreactor 206 and passed via line 208 to line 124 for ethanol recovery. Depleted gas phase is withdrawn from the top of bioreactor 206 via line 136.

Figure 3:
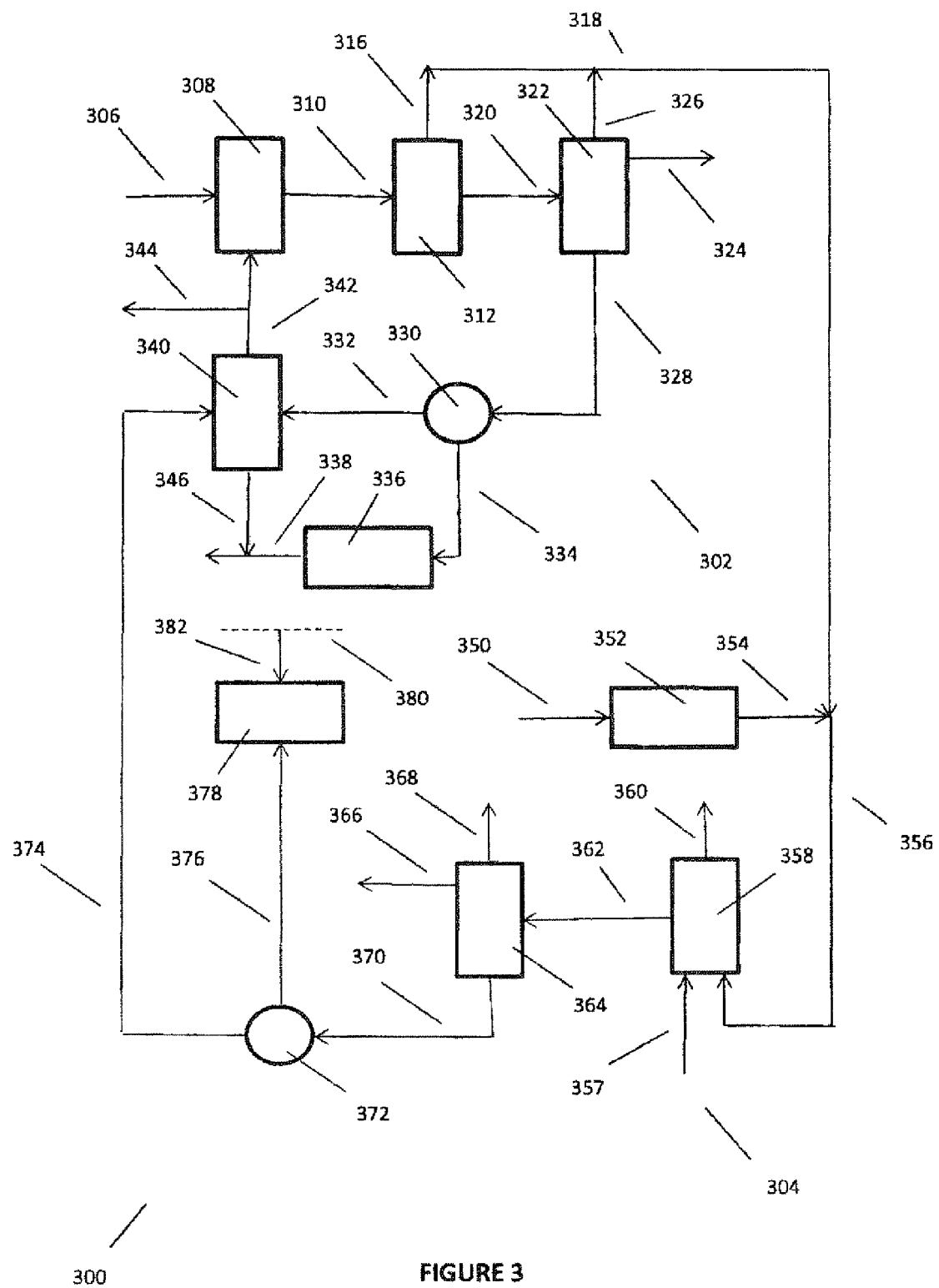
FIG. 3 is a schematic depiction of an integrated carbohydrate ethanol and anaerobic combined gas substrate, bioconversion facility.

FIG. 3 is a schematic, simplified depiction of apparatus 300 containing an integrated corn ethanol facility 302 and combined gas substrate to ethanol facility 304. Corn and water are passed via line 306 to hydrolyzer 308 where the starches in the corn are broken down to sugars for fermentation. The hydrolyzate generated in hydrolyzer 308 is passed via line 310 to fermentation vessel 312 containing a fermentation broth using yeasts to convert the sugars to ethanol and carbon dioxide. Evolved carbon dioxide which is usually vented or discarded is passed via line 316 to carbon dioxide header 318. The fermentation broth is passed via line 320 into beer still 322. Beer still 322 separates, by distillation, an ethanol product which exits via line 324. A lights fraction exits there still 322 via line 326 which is carbon dioxide header 318.

Beer still 322 has a solids and liquid-containing bottoms fraction, also known as the whole stillage. The whole stillage is withdrawn and passed via line 328 to centrifuge 330 to provide a thin stillage which exits via line 332 and wet distillers grains which exits via line 334. The wet distillers grains are passed to dryer 336 to provide dried distillers grains which are conveyed via line 338. Returning to the thin stillage in line 332, it is passed to the evaporator train 340. Evaporator train 340 has a plurality of evaporators and provides an overhead stream that is essentially water vapor which exits via line 342. The water vapor can be condensed and passed to hydrolyzer 308, as shown, or to fermentation vessel 312 (not shown.) If desired, a portion of the water may be withdrawn via line 344 for use, e.g., in combined gas substrate to ethanol facility 304 (not shown.) Evaporator train 340 also provides a concentrated sugar stream which exits via line 346 and can be combined with the dried distillers grains (not shown) to provide dried distillers grains with solubles.

With respect to the combined gas substrate to ethanol facility 304, natural gas is provided via line 350 to steam reformer 352. Reformed gas from steam reformer 352 exits via line 354 where it is combined with carbon dioxide from carbon dioxide header 318. The combined gases are passed via line 356 to a bubble column bioreactor 358. The combined gases have an electron to carbon atom ratio of between about 5.5:1 to 6.5:1. A depleted gas phase is withdrawn via line 360 from bioreactor 358. The depleted gas phase may be used as fuel for the hotbox of steam reformer 352 (not shown.) Some of the aqueous menstruum in bioreactor 358 is withdrawn a stream for recovery of ethanol which is passed by line 362 to distillation assembly 364. Line 357 supplies make-up water to replenish aqueous menstruum removed for product recovery. The make-up water may contain nutrients and other adjuvants for the anaerobic fermentation, and may also contain microorganisms for the bioconversion. Distillation assembly 364 provides an ethanol product stream via line 366, a lights stream which exits via line 368 and a stream containing solids and water which exits via line 370.

The solids and water stream in line 370 is sent to centrifuge 372. Centrifuge 372 provides a clear water-containing stream that also contains dissolved salts. This clear water-containing stream is passed via line 374 to evaporator train 340 where water vapor is separated from salts containing concentrate.

A concentrated solids-containing fraction generated by centrifuge 372 is passed via line 376 to aerobic digester 378. Aerobic digester 378 is also servicing the corn ethanol facility 302. Wastewater from corn ethanol facility 302 is collected at various points through collector 380 and is passed via line 382 to aerobic digester 378. The solids provided by line 376 contain cell debris which contributes to the nitrogen source for the aerobic digester.

Figure 4:
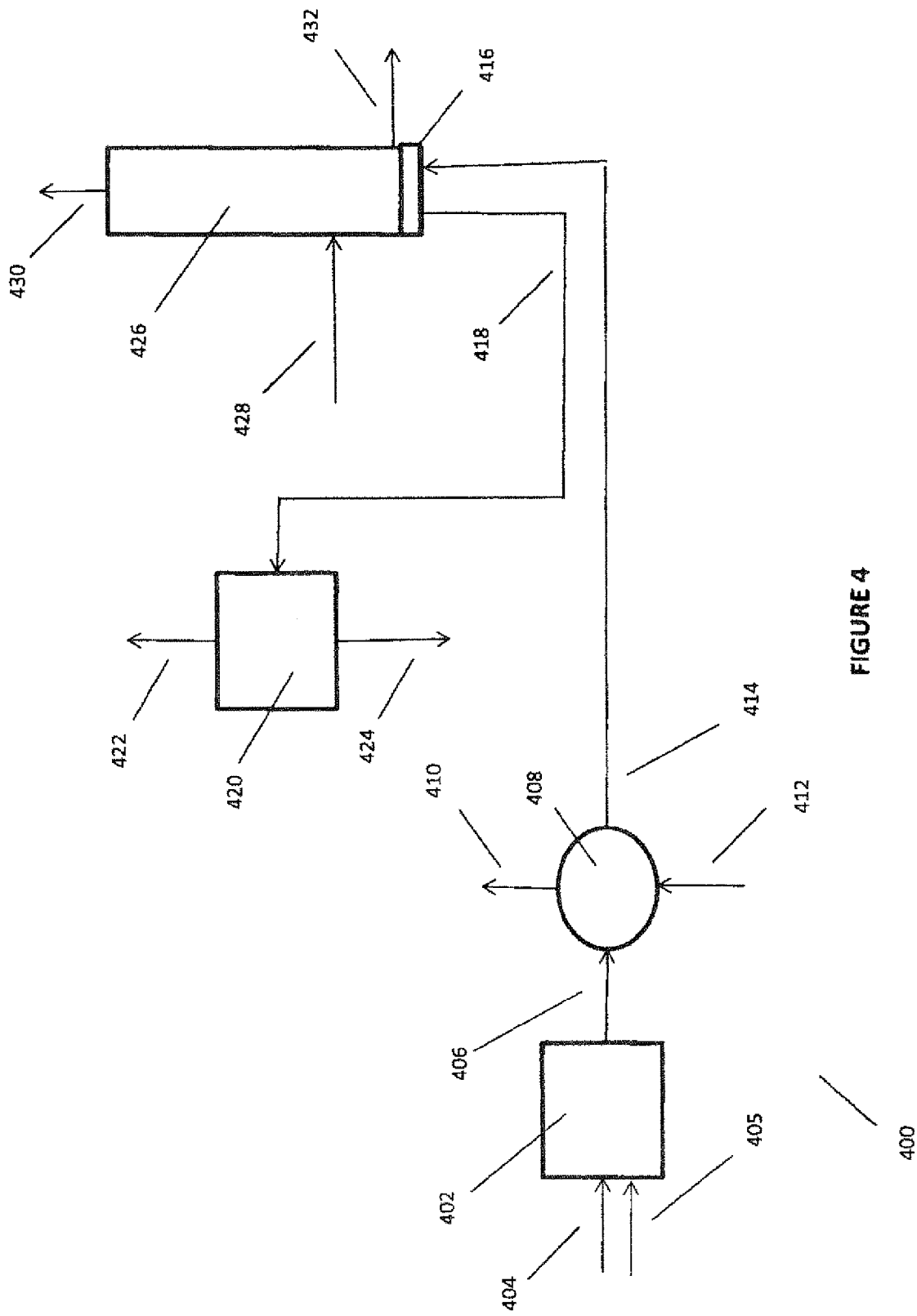
FIG. 4 is a schematic depiction of an integrated waste heat boiler from reformed gas generation and distillation reboiler for recovery of alcohol from aqueous menstruum.

FIG. 4 is a schematic depiction of an integration of unit operations generally designated by the number 400 to recover latent heat from reformed gas exiting a waste heat boiler for recovering heat from a reformer, and using the recovered heat in a distillation reboiler recovering alcohol. A steam reformer 402, and also an autothermal reformer where applicable, is provided with the hydrocarbonaceous feedstock via line 404. If any of the gas is supplied by an autothermal reformer, oxygen which may be pure oxygen, air or oxygen-enriched air is provided by line 405. Reformate exits via line 406 and is passed via line 406 to waste heat boiler 408 which generates steam at a pressure of about 950 kPa (absolute). The steam exits via line 410. Water is provided to waste heat boiler 408 via line 412. The cooled reformed gas contains about 33 volume percent water vapor and is at a temperature of about 128° C. and is passed via line 414 to distillation reboiler 416 which provides heat for distillation in distillation column 426. The reformed gas then passes to knock out vessel 420 via line 418 where condensate is removed. The reformed gas exiting knock out vessel 420 via line 422 contains about 12 volume percent water vapor and is at a temperature of about 104° C. Condensate exits knock out vessel 420 via line 424.

The reformed gas is used in an anaerobic fermentation to produce alcohol. Aqueous menstruum containing alcohol is passed to distillation column 426 via line 428. Alcohol, in particular, ethanol exits distillation column 426 via line 430 and an aqueous bottoms stream is removed from distillation column 426 via line 432.

Figure 5:
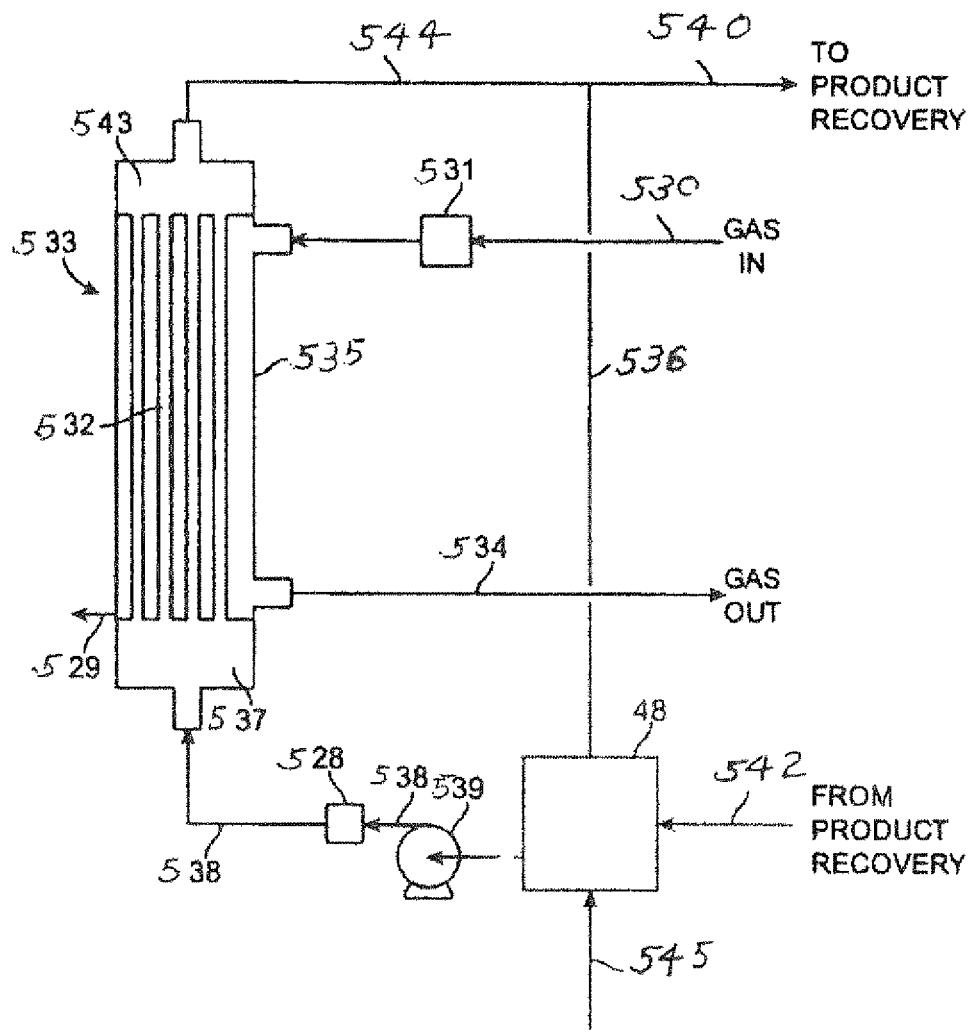
FIG. 5 is a schematic drawing of a membrane bioreactor system showing gas and liquid circulation.

FIG. 5 illustrates a specific configuration of a bio-reactor assembly utilizing a membrane supported bioreactor (MSBR) containing microorganisms. A gas supply conduit 530 delivers a substrate at a rate recorded by a flow meter 531 to a bioreactor 533. The bioreactor 533 includes a vessel 535 that surrounds the outside of the single module comprising membrane elements 532. Membrane elements 532 contain biopores to promote growth and maintenance of microorganisms within a biolayer on the outside of the membrane elements.

The MSBR process uses asymmetric membranes in a hollow fiber configuration, suitable for permeation of the fermentation liquid, that provides the separation between the menstruum and the substrate and further explained in U.S. Pat. No. 8,329,456 (issued Dec. 11, 2012 and herein incorporated by reference in its entirely). A feed gas distribution chamber 535 receives the feed gas stream and distributes it into direct contact with the outer surface of the membrane elements 532. The feed gas exits the vessel 535 via a line 534 such that a continuous addition of feed gas is established around the outer surface of membrane elements 532. The relative locations of the substrate feed line provides a downward direction of the bulk gas flow in the bioreactor 533.

Vessel 535 also contains a line 529 for draining liquid. Liquid may accumulate at the bottom of the vessel 535 for a variety of reasons such as condensation from moisture in the substrate, flushing or purging of the membrane elements or periodic cleaning operations. Fermentation liquid enters bioreactor 533 via a conduit 538 under pressure supplied by a pump 539 and at rate recorded by a flow meter 528. A chamber 537 distributes fermentation liquid to the tubular membranes 532 via the bottom ends of the lumens. At the top end of bioreactor 533 a chamber 543 collects the fermentation liquid from the top of the lumens for withdrawal of the liquid via a conduit 544. The relative locations of chambers 537 and 543 establish upward flow of the liquid through bioreactor 533 so that there is countercurrent flow with respect to the bulk gas flow and the liquid flow.

A line 540 withdraws a net portion of the liquid from line 544 while the remainder of the liquid returns to the bioreactor 533 via a recirculation line 536, mixing chamber 548, and a line 538. Line 540 carries the liquid to product recovery facilities that recover liquid products. Depending on the nature of the desired product, there are a number of technologies that can be used for product recovery. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products. In all cases the product recovery step removes the desirable product from stream 540, while leaving substantial amounts of water and residual nutrients in the treated stream as menstruum, part of which is returned to the bioreactor assembly via line 542 and mixing chamber 548.

Means for temperature and pH control for the liquid can be added anywhere along the re-circulating liquid loop, which consists of lines 538, 544, and 536 as well as chambers 537, 543, and 548. A line 545 provides the nutrients needed to sustain the activity of the microorganisms to the re-circulating liquid loop trough chamber 548. Chamber 548 provides mixing of the nutrients and the other streams.

The flow rates of Streams 538 and 544, recirculated through the membrane unit, are selected so that there is no significant liquid boundary layer that impedes mass transfer near the liquid-facing side of the membrane. The superficial linear velocity of the liquid tangential to the membrane should be in the range of 0.01 to 20 cm/s, preferably 0.05 to 5 cm/s, and most preferably 0.2 to 1.0 cm/s.

It is claimed:

1. A process for deriving an alcohol from the anaerobic bioconversion of a gas substrate comprising:
    a) steam reforming a carbonaceous gas from a non-renewable source to produce a reformed gas having an electron carbon ratio of greater than 7:1 and at least 90% of the available electrons from the methane in the carbonaceous gas;
    b) combining the reformed gas a with renewable gas derived from a renewable carbon source to provide a gas substrate comprising hydrogen, carbon monoxide, and carbon dioxide in which between about 20 and 70 percent of the carbon in the gas substrate is from renewable carbon in the renewable gas, the balance of the gas substrate stream is made from non-renewable carbon in the reformed gas, and the electron to carbon (e/C) ratio of the gas substrate is in a range from 5.5:1 to 6.7:1;
    c) continuously contacting said substrate gas with an aqueous menstruum containing anaerobic microorganisms to bioconvert the substrate gas to alcohol and provide an alcohol-containing menstruum and a substrate depleted gas phase, wherein said contacting is in a bioreactor assembly containing said menstruum;
    d) continuously withdrawing a substrate depleted gas phase from said aqueous menstruum, said depleted gas phase having a lower mass quantity of CO2 than the mass quantity of CO2 in the combined gas stream; and,
    e) continuously or intermittently withdrawing a portion of said menstruum for recovery of said alcohol, said withdrawal being sufficient to maintain the alcohol in said menstruum below a concentration that unduly adversely affects the microorganisms.

2. The process of claim 1 wherein the bioconversion of the gas substrate to alcohol converts at least about 85 mole percent of hydrogen and carbon oxides in the gas substrate.

3. The process of claim 1 in which between about 30 and 50 percent of the carbon in the gas substrate is from renewable carbon.

4. The process of claim 1 wherein said steam reforming is performed in a steam reformer having at least one gas reforming section and at least one hotbox section and at least a portion of the depleted gas phase is passed to the hotbox section of the steam reformer.

5. The process of claim 1 wherein said reformed gas and said renewable gas comprise at least about 25 mole percent carbon dioxide, said renewable gas having an electron to carbon ratio not greater than about 0.1:1 to provide an overall gas substrate having an electron to carbon ratio in the range of about 5.5:1 to 6.5:1.

6. The process of claim 1 wherein the mole ratio of carbon dioxide to methane in the depleted gas phase is less than about 0.2:1.

\* \* \* \* \*